United States Patent
Lin et al.

(10) Patent No.: US 10,624,941 B2
(45) Date of Patent: Apr. 21, 2020

(54) **METHOD FOR REGULATING EXPRESSIONS OF *NOS3* GENE, *PLAT* GENE, *F3* GENE AND/OR *SERPINE1* GENE BY USING *CHENOPODIUM FORMOSANUM* EXTRACT**

(71) Applicant: TCI CO., LTD., Taipei (TW)

(72) Inventors: Yung-Hsiang Lin, Taipei (TW); I-Hui Chen, Taipei (TW); Yu-Ting Cheng, Taipei (TW)

(73) Assignee: TCO Co., Ltd., Taipei (TW)

( * ) Notice: Subject to any disclaimer, the term of this patent is extended or adjusted under 35 U.S.C. 154(b) by 104 days.

(21) Appl. No.: 15/843,398

(22) Filed: Dec. 15, 2017

(65) Prior Publication Data

US 2018/0169164 A1 Jun. 21, 2018

Related U.S. Application Data

(60) Provisional application No. 62/435,613, filed on Dec. 16, 2016.

(51) Int. Cl.
| | | |
|---|---|---|
| *A61K 36/21* | (2006.01) | |
| *A61P 7/02* | (2006.01) | |
| *A61P 25/00* | (2006.01) | |
| *A61P 3/04* | (2006.01) | |
| *A61P 17/00* | (2006.01) | |
| *A61P 9/00* | (2006.01) | |

(52) U.S. Cl.
CPC ............... *A61K 36/21* (2013.01); *A61P 3/04* (2018.01); *A61P 7/02* (2018.01); *A61P 9/00* (2018.01); *A61P 17/00* (2018.01); *A61P 25/00* (2018.01)

(58) Field of Classification Search
None
See application file for complete search history.

(56) References Cited

U.S. PATENT DOCUMENTS

| | | | | |
|---|---|---|---|---|
| 8,455,017 | B2 * | 6/2013 | Tsai | A61K 36/21 424/725 |
| 2015/0265527 | A1 * | 9/2015 | Su | A61K 8/97 424/725 |

FOREIGN PATENT DOCUMENTS

CN 104922171 A 9/2015

OTHER PUBLICATIONS

Kaul (Journal of the National Medical Association (1993), vol. 85, No. 3, pp. 231-232).*
Danielsson, "Causes and Risk of Stillbirth," Sep. 2019. Accessed on line at https://www.verywellfamily.com/intrauterine-fetal-demise-2371631?print.*
Shih, Pin-Tsen ,"Immunomodulatory Activity of Polysaccharides Isolated from Chenopodium Formosanum Koidz in Macrophage Model", National Pingtun University of Science and Technology Department of Food Science, Taiwan, pp. 1-10, 13, 16-20 and 49-54, with English abstract (33 pages). 2012.
"Red Quinoa," *Medicinal Plant Theme Pavilion*, 11 pages (Nov. 10, 2014).
Ladenvall, P., et al., "Genetic variation at the human tissue-type plasminogen activator (tPA) locus: haplotypes and analysis of association to plasma levels of tPA," *European Journal of Human Genetics*, vol. 11, pp. 603-610 (2003).
Gangaraju, Radhika, et al., "Upregulation of Thrombo-Inflammatory Pathways May Contribute to Increased Thrombotic Risk in Polycythemia Vera and Essential Thrombocythemia," *Blood*, vol. 128, No. 22 3143, 6 pages (Dec. 1, 2016).
Merx, Marc W., et al., "Depletion of circulating blood NOS3 increases severity of myocardial infarction and left ventricular dysfunction," *Basic Res Cardiol*, 109:398, 10 pgs. (2014).
Shamseldin, Hanan E., et al., "A lethal phenotype associated with tissue plasminogen deficiency in humans," *Hum Gent*, 135(10), 3 pgs. (2016).
Yang, Minxia, et al., "The role of mononuclear cell tissue factor and inflammatory cytokines in patients with chronic thromboembolic pulmonary hypertension," *J Thromb Thrombolysis*, vol. 42, pp. 38-45 (2016).
Zebrowska, Agnieszka, et al., "Tissue Factor in Dermatitis Herpetiformis and Bullous Pemphigoid: Link between Immune and Coagulation System in Subepidermal Autoimmune Bullous Diseases," *Mediators of Inflammation;*, vol. 2015, Hindawa Publishing Corporation, 9 pgs. (2015).
Vaughan, Douglas E., et al., "Plasminogen Activator Inhibitor-1 is a Marker and a Mediator of Senescence," *Arterioscler Throm Vasc Biol*, 8 pgs. See http:// at atvb.ahajournals.org/content/early/2017/06/01/ATVBAHA.117.309451 (Jun. 1, 2017).
Gazioglu, Sema Bilgic, et al., "PAI-1 and TNF-α profiles of adipose tissue in obese cardiovascular disease patients," *Int J Clin Exp Pathol*, 8(12), pp. 15919-15925 (2015).

* cited by examiner

*Primary Examiner* — Susan Hoffman
(74) *Attorney, Agent, or Firm* — Christensen, Fonder, Dardi & Herbert PLLC

(57) ABSTRACT

A method for increasing expression of NOS3 gene, increasing expression of PLAT gene, decreasing expression of F3 gene and/or decreasing expression of SERPINE1 gene is provided, wherein the method comprises administering to a subject in need an effective amount of a *Chenopodium formosanum* extract. Accordingly, the method is effective in treating or preventing diseases associated with NOS3 gene, PLAT gene, F3 gene and/or SERPINE1 gene.

4 Claims, 2 Drawing Sheets

METHOD FOR REGULATING EXPRESSIONS OF *NOS3* GENE, *PLAT* GENE, *F3* GENE AND/OR *SERPINE1* GENE BY USING *CHENOPODIUM FORMOSANUM* EXTRACT

FIELD OF THE INVENTION

The present invention relates to the uses of *Chenopodium formosanum* extract, particularly a water extract of *Chenopodium formosanum*, in treating or preventing diseases associated with the NOS3 gene, PLAT gene, F3 gene, and/or SERPINE1 gene. The present invention especially relates to the uses of the extract in at least one of inhibiting thrombosis, decomposing thrombus, and regulating blood pressure.

BACKGROUND OF THE INVENTION

Hemostasis is crucial to the survival of organisms; however, abnormal blood coagulation and abnormal thrombosis can easily result in diseases with a high mortality rate, such as vein thrombosis, pulmonary embolism, stroke, myocardial infarction, and hypertension. There are many reasons for the formation of an abnormal or excessive thrombus, wherein the most common reasons include, for example, endothelial damage in blood vessels, blood stasis, and excessive blood clotting. Patients who suffer from heart disease, hypertension, high level of blood lipids, diabetes mellitus, or cancer, and people who sit for a long time or do not get enough exercise, are at high risk for thrombus-related diseases.

Currently, the primary approach adopted in clinic for treating thrombus-related diseases is to administer thrombolytic drugs (e.g., tissue-type plasminogen activator (tPA)) or anticoagulants (e.g., heparin and warfarin) to the patient. However, the thrombolytic drugs that are currently used put patients at risk of bleeding disorders and cannot lyse a bigger thrombus, and the current anticoagulants cannot reduce the size of a formed thrombus. Therefore, there is a necessity and urgency for continuously developing a drug or a method for inhibiting thrombosis and/or decomposing thrombus effectively without causing side effects.

Researchers have found that thrombosis and thrombolysis are regulated by genes such as NOS3, PLAT, F3, and SERPINE1, wherein (1) an overexpression of the F3 gene and SERPINE1 gene can lead to thrombosis, (2) an increased expression of PLAT gene can promote the decomposition of a formed thrombus, and (3) an increased expression of NOS3 gene can promote vasodilatation and reduce platelet accumulation and thus is helpful for regulating blood pressure and inhibiting thrombosis. Accordingly, one may effectively regulate blood pressure, inhibit thrombosis and/or decompose thrombi by increasing the expression of NOS3 gene, increasing the expression of PLAT gene, decreasing the expression of F3 gene, and/or decreasing the expression of SERPINE1 gene.

Inventors of the present invention found that *Chenopodium formosanum* extract is effective in regulating the expressions of NOS3, PLAT, F3, and SERPINE1 genes, and thus, can be used for inhibiting thrombosis, decomposing thrombus, assisting in regulation of blood pressure as well as for treating or preventing the diseases associated with the aforementioned genes.

SUMMARY OF THE INVENTION

An objective of the present invention is to provide a use of a *Chenopodium formosanum* extract in the manufacture of a composition, wherein the composition is used for at least one of increasing the expression of NOS3 gene, increasing the expression of PLAT gene, decreasing the expression of F3 gene, and decreasing the expression of SERPINE1 gene. Preferably, the *Chenopodium formosanum* extract is a water extract of *Chenopodium formosanum*. The composition is a pharmaceutical composition or a food composition.

The pharmaceutical composition provided in accordance with the present invention is used for at least one of treating cardiovascular diseases (including myocardial infarction, left ventricular dysfunction, chronic thromboembolic pulmonary hypertension, hypertension, and thrombus), treating hydranencephaly, treating bullous pemphigoid, treating obesity, preventing cardiovascular diseases, preventing hydranencephaly, preventing bullous pemphigoid, preventing obesity, preventing fetal death, and delaying aging. Especially, the pharmaceutical composition is used for inhibiting thrombosis and/or decomposing thrombus. Preferably, the pharmaceutical composition is provided in a form for oral administration, intravenous injection, or subcutaneous injection.

The food composition provided in accordance with the present invention is used for assisting in inhibition of thrombosis, decomposition of thrombus and/or regulation of blood pressure. Preferably, the food composition is a health food, a dietary supplement, a functional food, a nutritional supplement food or a special nutritional food. More preferably, the food composition is provided as dairy products, meat products, breadstuff, pasta, cookies, troche, capsules, fruit juices, teas, sports beverages, or nutrient beverages.

Another objective of the present invention is to provide a method for increasing the expression of NOS3 gene, increasing the expression of PLAT gene, decreasing the expression of F3 gene and/or decreasing the expression of SERPINE1 gene, comprising administering to a subject in need an effective amount of a *Chenopodium formosanum* extract. Preferably, the extract administered to the subject in need is a water extract of *Chenopodium formosanum*. The method is for at least one of treating cardiovascular diseases (including myocardial infarction, left ventricular dysfunction, chronic thromboembolic pulmonary hypertension, hypertension, and thrombus), treating hydranencephaly, treating bullous pemphigoid, treating obesity, preventing cardiovascular diseases, preventing hydranencephaly, preventing bullous pemphigoid, preventing obesity, preventing fetal death, and delaying aging. Preferably, the method is for inhibiting thrombosis and/or decomposing thrombus.

The detailed technology and some of the embodiments implemented for the present invention are described in the following paragraphs for persons skilled in the art to well appreciate the features of the claimed invention.

DESCRIPTION OF THE PREFERRED EMBODIMENT

Figure 1:
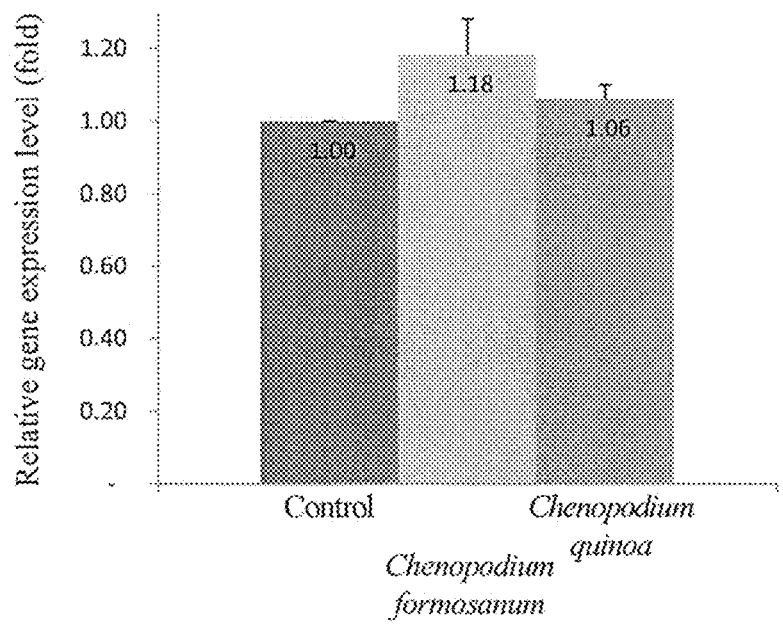
FIG. 1 shows that, in comparison with the control group, the expression level of NOS3 gene in the HUVEC cells of "*Chenopodium formosanum* group" or "*Chenopodium quinoa* group," wherein the cells in "control group" was cultured in a medium containing neither *Chenopodium formosanum* extract nor *Chenopodium quinoa* extract for 24 hours, and those in "*Chenopodium formosanum* group" and "*Chenopodium quinoa* group" are respectively cultured in a medium containing *Chenopodium formosanum* extract and in a medium containing *Chenopodium quinoa* extract for 24 hours.

The following paragraphs will describe some of the embodiments of the present invention in detail. However, without departing from the spirit of the present invention, the present invention may be embodied in various embodiments and should not be limited to the embodiments described in the specification and the appended claims.

Unless otherwise indicated herein, the expression "a," "an," "the," or the like recited in the specification of the present invention (especially in the claims) are intended to include both the singular and plural forms. The term "treat", or "treating" recited in this specification should not be construed as treating a subject until the subject is completely recovered, but should include maintaining the progression or symptoms of the diseases in a substantially static state, increasing the recovery rate of a subject, alleviating the severity of a particular condition of illness, or enhancing the quality of life of a patient. The term "prevent" or "preventing" recited in this specification refers to inhibiting or preventing a particular condition of illness from breaking out, or maintaining the ability to tolerate diseases in a sensitive subject in good health. The term "regulate", "regulating" or "regulation" recited in this specification refer to upregulating (including inducing, stimulating, and enhancing) or downregulating (including inhibiting, and weakening) the physiological functions in a subject towards the normal state. The term "regulation of blood pressure" or "regulating blood pressure" recited in this specification refers to changing the value of blood pressure towards the normal value. The term "an effective amount" recited in this specification refers to the amount of the substance that can at least partially alleviate the condition that is being treated in a suspected subject when administered to the subject. The term "subject" recited in this specification refers to a mammalian, including human and non-human animals.

The *Chenopodium formosanum* adopted in accordance with the present invention, also known as Taiwan quinoa, is a native plant in Taiwan with great nutritional value and is a traditional grain crop for the Taiwanese aborigines. *Chenopodium quinoa*, also known as quinoa, which originates from America, is used as a control group in the appended examples. Though *Chenopodium formosanum* and *Chenopodium quinoa* are different in both appearance and nutritional ingredients, people often confuse them due to their similar names.

As indicated above, inventors of the present invention found that the *Chenopodium formosanum* extract is effective in regulating the expressions of genes such as NOS3, PLAT, F3, and SERPINE1. Among these genes, it has been known that a decreased expression of NOS3 gene is involved in myocardial infarction and left ventricular dysfunction. Therefore, if the expression of NOS3 gene can be increased, the myocardial infarction and left ventricular dysfunction can be treated or prevented. The correlation between NOS3 gene and myocardial infarction as well as left ventricular dysfunction can be noted from such as "Depletion of circulation blood NOS3 increases severity of myocardial infarction and left ventricular dysfunction. *Basic Res Cardiol.* 109(1): 398 (2014)", which is entirely incorporated hereinto by reference.

It has been known that a decreased expression of PLAT gene is involved in thrombosis, hydranencephaly and fetal death. Therefore, if the expression of the PLAT gene can be increased, thrombosis and hydranencephaly can be treated or prevented and the fetal death can be prevented. The correlation between PLAT gene and thrombosis, hydranencephaly as well as fetal death can be noted from such as "A lethal phenotype associated with tissue plasminogen deficiency in humans. *Hum Genet.* 135(10): 1209-11 (2016)", which is entirely incorporated hereinto by reference.

It has been known that an overexpression of F3 gene is involved in thrombus, chronic thromboembolic pulmonary hypertension and bullous pemphigoids. Therefore, if the expression of the F3 gene can be decreased, thrombus, chronic thromboembolic pulmonary hypertension and bullous pemphigoids can be treated or prevented. The correlation between F3 gene and thrombus, chronic thromboembolic pulmonary hypertension as well as bullous pemphigoids can be noted from such as "The role of mononuclear cell tissue factor and inflammatory cytokines in patients with chronic thromboembolic pulmonary hypertension. *J Thromb Thrombolysis.* 42(1): 38-45 (2016);" and "Tissue Factor in Dermatitis Herpetiformis and Bullous Pemphigoid: Link between Immune and Coagulation System in Subepidermal Autoimmune Bullous Disease. *Mediators of Inflammation.* 2015, Aritcle ID 870428, 9 pages", which are entirely incorporated hereinto by reference.

An overexpression of SERPINE1 gene is involved in aging, obesity and cardiovascular diseases (including thrombus). Therefore, if the expression of SERPINE1 gene can be decreased, obesity and cardiovascular diseases can be treated or prevented, and aging can be delayed. The correlation between SERPINE1 gene and aging, obesity as well as cardiovascular diseases can be noted from such as "Plasminogen Activator Inhibiyor-1 Is a Marker and a Mediator of Senescence. *Arterioscler Thromb Vasc Biol.* 37(8): 1446-1452 (2017);" and "PAI-1 and TNF-α profiles of adipose tissue in obese cardiovascular disease patients. *Int J Clin Exp Pathol* 8(12): 15919-15925 (2015)", which are entirely incorporated hereinto by reference.

Thus, the present invention provides a use of *Chenopodium formosanum* extract in the manufacture of a composition, wherein the composition is used for increasing expression of NOS3 gene, increasing expression of PLAT gene, decreasing expression of F3 gene and/or decreasing expression of SERPINE1 gene. The composition can be provided as a pharmaceutical composition or a food composition. The pharmaceutical composition provided in accordance with the present invention is used for at least one of treating cardiovascular diseases (including myocardial infarction, left ventricular dysfunction, chronic thromboembolic pulmonary hypertension, hypertension, and thrombus), treating hydranencephaly, treating bullous pemphigoid, treating obesity, preventing cardiovascular diseases (including myocardial infarction, left ventricular dysfunction, chronic thromboembolic pulmonary hypertension, hypertension, and thrombus), preventing hydranencephaly, preventing bullous pemphigoid, preventing obesity, preventing fetal death, and delaying aging. Especially, the pharmaceutical composition provided in accordance with the present invention is used for inhibiting thrombosis and/or decomposing thrombus. The food combination provided in accordance with the present invention is used for assisting in inhibition of thrombosis, decomposing thrombus and/or regulation of blood pressure.

The *Chenopodium formosanum* extract in accordance with the present invention can be provided by a method comprising the following steps: (a) extracting *Chenopodium formosanum* with a polar solvent to provide a crude extract solution; (b) centrifuging the crude extract solution and filtering the supernatant thus obtained to provide a filtrate; and (c) concentrating the filtrate by vacuum to obtain a concentrated extract solution (i.e., the *Chenopodium formosanum* extract of the present invention). Furthermore, the *Chenopodium formosanum* adopted by the present invention can be dehulled or un-dehulled.

In step (a), the polar solvent can be selected from the group consisting of water, alcohol (e.g., C1-C4 alcohols), and combinations thereof. The amount of the polar solvent and *Chenopodium formosanum* can be optionally adjusted. In general, there is no limitation of the amount of polar solvent as long as the raw materials can be evenly dispersed in the polar solvent. For example, in step (a), the polar solvent and *Chenopodium formosanum* can be used at a volume ratio ranging from about 1:1 to about 20:1 (polar solvent: *Chenopodium formosanum*). In one embodiment of the present invention, step (a) was carried out with the use of water as the polar solvent at a volume ratio of 10:1 (water: *Chenopodium formosanum*).

In step (a), the extraction can be conducted for a suitable period of time depending on the polar solvent being adopted. For example, when water is used as the polar solvent at a volume ratio of 10:1 (water: *Chenopodium formosanum*), the extraction is usually conducted for at least 0.5 hour, preferably at least 1.5 hours, and more preferably at least 3 hours. In addition, the extraction in step (a) can be optionally accompanied with other operations such as heating, cooling and ultrasonication. For example, step (a) can be conducted at a temperature ranging from 50° C. to 100° C. In one embodiment of the present invention, step (a) was conducted at 75° C. for 0.5 hour. Moreover, *Chenopodium formosanum* can be optionally crushed, ground and/or cut to become particles with size as small as possible prior to conducting step (a), to enhance the extraction efficiency.

In step (c), the temperature for the vacuum-concentration can be optionally adjusted. For example, the vacuum-concentration of step (c) can be conducted at a temperature ranging from 45° C. to 70° C. In one embodiment of the present invention, the vacuum-concentration of step (c) was conducted at 60° C. The *Chenopodium formosanum* extract adopted in accordance with the present invention can also be a dry matter provided by drying the concentrated extract solution obtained from step (c). To achieve an extraction efficiency as high as possible, optionally, the *Chenopodium formosanum* can be repeated extracted with the same or different polar solvents prior to step (b) and the extracts thus obtained are combined to provide the crude extract solution for use in step (b); also, the step (b), the step (c), and/or the cycle of other operations described above can be repeated.

Depending on the desired purpose, the pharmaceutical composition in accordance with the present invention can be provided in any suitable form without special limitations. For example, the pharmaceutical compositions can be administered to a subject in need by an oral or parenteral (e.g., subcutaneous or intravenous) route. Depending on the form and purpose, suitable carriers could be chosen and used to provide the pharmaceutical composition, wherein the carriers include excipients, diluents, auxiliaries, stabilizers, absorbent retarders, disintegrating agents, hydrotropic agents, emulsifiers, antioxidants, adhesives, binders, tackifiers, dispersants, suspending agents, lubricants, hygroscopic agents, etc.

As a dosage form for oral administration, the pharmaceutical composition provided in accordance with the present invention can comprise any pharmaceutically acceptable carrier that will not adversely affect the desired effects of the active ingredients (i.e., *Chenopodium formosanum* extract), such as water, saline, dextrose, glycerol, ethanol or its analogs, cellulose, starch, sugar bentonite, and combinations thereof. The pharmaceutical composition can be provided in any suitable form for oral administration, such as in the form of a tablet (e.g., dragees), a pill, a capsule, granules, a pulvis, a fluidextract, a solution, a syrup, a suspension, a tincture, etc.

As for the form of injections or drips suitable for subcutaneous injection or intravenous injection, the pharmaceutical composition provided in accordance with the present invention can comprise one or more ingredient(s), such as an isotonic solution, a salt-buffered saline (e.g., phosphate-buffered saline or citrate-buffered saline), a hydrotropic agent, an emulsifier, a 5% sugar solution, and other carriers to provide the pharmaceutical composition as an intravenous infusion, an emulsified intravenous infusion, a powder for injection, a suspension for injection, or a powder suspension for injection, etc. Alternatively, the pharmaceutical composition can be prepared as a pre-injection solid. The pre-injection solid can be provided in a form which is soluble in other solutions or suspensions, or in an emulsifiable form. A desired injection is provided by dissolving the pre-injection solid in other solutions or suspensions or emulsifying it prior to being administered to a subject in need.

Depending on the need, age, body weight, and health conditions of the subject, the pharmaceutical composition provided in accordance with the present invention can be administered at various frequencies, such as once a day, multiple times a day, or once every few days, etc. The ratio of amount of *Chenopodium formosanum* extract in the composition provided in accordance with the present invention can be adjusted depending on the requirements of practical application. In addition, the pharmaceutical composition can optionally further comprise one or more other active ingredient(s) (e.g., plasminogen activator, heparin, and warfarin, etc.), or to be used in combination with a medicament comprising one or more other active ingredient(s), to further enhance the effects of the pharmaceutical composition, or to increase the application flexibility and application adaptability of preparation thus provided, as long as the other active ingredients do not adversely affect the desired effects of the active ingredients of the present invention (i.e., *Chenopodium formosanum* extract).

Optionally, the pharmaceutical composition or food composition provided in accordance with the present invention can further comprise a suitable amount of additives, such as a flavoring agent, a toner, or a coloring agent for enhancing the palatability and the visual perception of the pharmaceutical composition or food composition, and/or a buffer, a conservative, a preservative, an antibacterial agent, or an antifungal agent for improving the stability and storability of the pharmaceutical composition or food composition.

The food combination provided in accordance with the present invention can be a health food, a dietary supplement, a functional food, a nutritional supplement food or a special nutritional food, and can be produced as dairy products, meat products, breadstuff, pasta, cookies, troche, capsules, fruit juices, teas, sports beverages, nutrient beverages, etc., but is not limited thereby. Preferably, the food composition provided in accordance with the present invention is a health food.

Depending on the need, age, body weight, and health conditions of the subject, the food composition provided in accordance with the present invention can be taken various frequencies, such as once a day, multiple times a day, or once every few days, etc. The amount of *Chenopodium formosanum* extract in the health food, dietary supplement, functional food, nutritional supplement food and special nutritional food provided in accordance with the present invention can be also adjusted, preferably to the amount that should be taken daily, depending on the specific population.

The recommended daily dosage, use standards and use conditions for a specific population (e.g., hypertension patients, stroke patients, pregnant woman, etc.), or the recommendations for a use in combination with another food product or medicament can be labeled on the exterior package of health food, dietary supplement, functional food, nutritional supplement food and/or special nutritional food, and thus, the users can take the health food, dietary supplement, functional food, nutritional supplement food and/or special nutritional food. Thus, it is suitable for the user to take the health food, dietary supplement, functional food, nutritional supplement food and/or special nutritional food by him- or herself safely and securely without the instructions of a doctor, pharmacist or related executive. In the food combination provided in accordance with the present invention, the type and uses in related applications of *Chenopodium formosanum* extract are all in line with the above descriptions.

The present invention also provides a method for increasing expression of NOS3 gene, increasing expression of PLAT gene, decreasing expression of F3 gene, and/or decreasing expression of SERPINE1 gene, comprising administering to a subject in need an effective amount of a *Chenopodium formosanum* extract. The type, applied route, applied form, applied frequency, and uses in the related applications of *Chenopodium formosanum* extract are all in line with the above descriptions.

The present invention will be further illustrated in detail with specific examples as follows. However, the following examples are provided only for illustrating the present invention and the scope of the present invention is not limited thereby. The scope of the present invention will be indicated in the appended claims.

EXAMPLES

Preparation Examples

A. Preparation of *Chenopodium formosanum* Extract

*Chenopodium formosanum* (habitat: Pingtung County, Taiwan) was subjected to the following steps to provide a *Chenopodium formosanum* extract:
1. Grinding *Chenopodium formosanum*, and then filtering the grinded *Chenopodium formosanum* with a 10-mesh filter to provide a *Chenopodium formosanum* powder;
2. Mixing the *Chenopodium formosanum* powder obtained from step 1 with water at a volume ratio of *Chenopodium formosanum* powder:water=1:10 and conducting an extraction at 75° C. for 0.5 hour to provide a crude extract solution;
3. Cooling the crude extract solution obtained from step 2 to room temperature, then centrifuging the same at a rotary speed of 5,000 rpm for 10 minutes and filtering the supernatant thus provided with a 400-mesh filter to provide a filtrate; and
4. Concentrating the filtrate obtained from step 3 by vacuum at 60° C. to provide a concentrated extract solution (i.e., a *Chenopodium formosanum* extract in accordance with the present invention).

B. Preparation of *Chenopodium quinoa*

*Chenopodium quinoa* (habitat: Chile) was subjected to an operation as mention in [Preparation example A] to provide a *Chenopodium quinoa* extract.

C. Treatment of Cells

Human umbilical vein endothelial cells (HUVEC; purchased from ATCC, product no.: CRT-1730) were seeded in 6-well plate ($1.5 \times 10^5$ cells/well) to conduct a cultivation for 24 hours, then, the cells were divided into the control group, *Chenopodium formosanum* group and *Chenopodium quinoa* group (three groups in total, and two repetitions for each group) and were cultivated in the following medium for 24 hours:
1. Control group: a F-12K medium containing 0.1 mg/ml heparin, 0.03-0.05 mg/ml endothelial cell growth supplement and 10% fetal bovine serum;
2. *Chenopodium formosanum* group: a medium same as that of the control group, but additionally added with 0.3125 mg/ml *Chenopodium formosanum* extract obtained from [Preparation Example A]; and
3. *Chenopodium quinoa* group: a medium same as that of the control group, but additionally added with 0.3125 mg/ml *Chenopodium quinoa* extract obtained from [Preparation Example B].

Thereafter, the cells of the above groups were harvested and subjected to a RNA extraction with an RNA Extraction Kit (purchased from Geneaid company). Then, the RNA thus obtained was transcribed into cDNA with a reverse transcriptase (SuperScript® III Reverse Transcriptase, purchased from Invitrogen). Thereafter, the above cDNA was subjected to qPCR (quantitative polymerase chain reaction) by a ABI Step One Plus system with a KAPA SYBR FAST kit to determine the expression levels of the vasodilatation-related genes (including NOS3), thrombolysis-related genes (including PLAT), and thrombosis-related genes (including F3 and SERPINE1) in the cells of each group. The relative gene expression level of each group was calculated by using the results of control group as a basis (i.e., the gene expression level of control group was served as 1-fold). The results are shown in Table 1, and FIG. 1 to FIG. 3.

TABLE 1

| | vaso-dilatation-related genes | thrombolysis-related genes | thrombosis-related genes | |
| --- | --- | --- | --- | --- |
| | NOS3 | PLAT | F3 | SERPINE1 |
| *Chenopodium formosanum* group (as compared to the gene expression level of control group) | 1.18* | 1.30* | 0.48** | 0.92 |
| *Chenopodium quinoa* group (as compared to the gene expression level of control group) | 1.06* | 0.99 | 0.56** | 1.00 |

P value:
*p < 0.05;
**p < 0.01

As shown in Table 1 and FIG. 1, in comparison with the control group, the cells of both *Chenopodium formosanum* group and *Chenopodium quinoa* group exhibited an increased expression level of NOS3 gene, and a much significant increase was observed in the *Chenopodium formosanum* group. These results indicate that *Chenopodium formosanum* extract in accordance with the present invention can increase the expression level of NOS3 gene, and thus, can promote vasodilatation and reduce platelet accumulation effectively, thereby achieving the effects of assisting in regulation of blood pressure and inhibition of thrombosis. Furthermore, the efficacy of *Chenopodium formosanum* extract is better than that of the *Chenopodium quinoa* extract.

Figure 2:
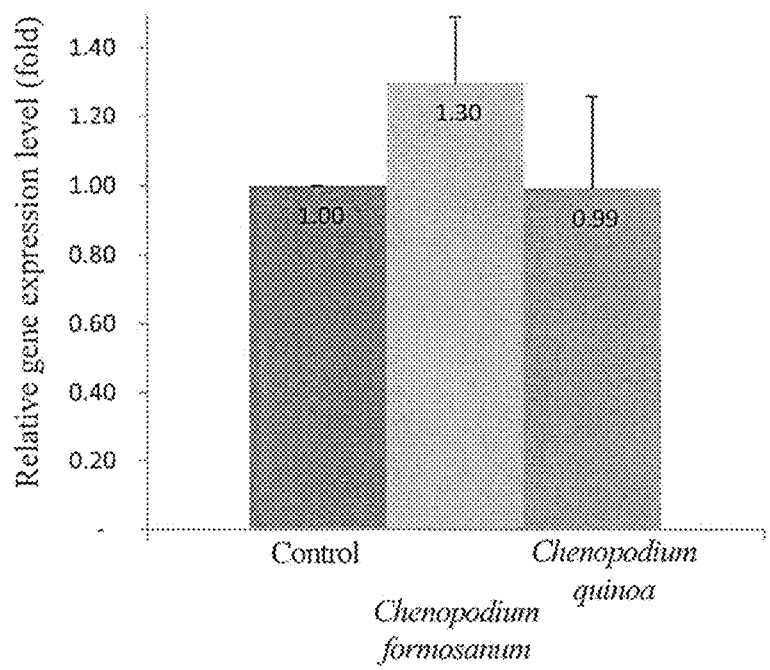
FIG. 2 shows that, in comparison with the control group, the expression level of PLAT gene in the HUVEC cells of "*Chenopodium formosanum* group" or "*Chenopodium quinoa* group"

As shown in Table 1 and FIG. 2, in comparison with the control group, the cells of *Chenopodium formosanum* group exhibited a significantly increased expression level of PLAT gene, while the cells of *Chenopodium quinoa* group did not. These results indicate that the *Chenopodium formosanum* extract in accordance with the present invention can increase the expression level of PLAT gene, and thus, can decompose the formed thrombus effectively. The *Chenopodium quinoa* extract, however, could not achieve the same effect as that of the *Chenopodium formosanum* extract in accordance with the present invention.

Figure 3:
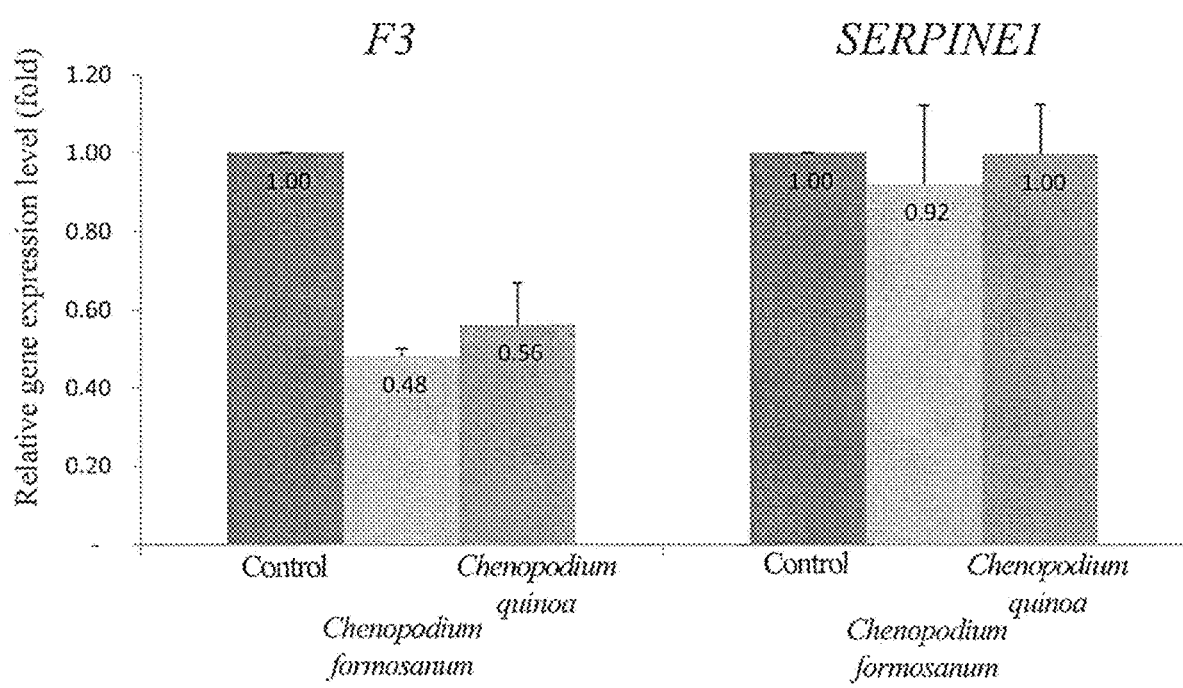
FIG. 3 shows that, in comparison with the control group, the expression levels of SERPINE1 gene and F3 gene in the HUVEC cells of "*Chenopodium formosanum* group" or "*Chenopodium quinoa* group".

As shown in Table 1 and FIG. 3, in comparison with the control group, the cells of *Chenopodium formosanum* group exhibited decreased expression levels of both F3 gene and SERPINE1 gene. In the cells of *Chenopodium quinoa* group, the expression level of F3 gene also decreased, while the expression level of SERPINE1 gene did not significantly change. These results indicate that the *Chenopodium formosanum* extract in accordance with the present invention can decrease the expression levels of F3 gene and SERPINE1 gene, and thus, can inhibit thrombosis effectively. The *Chenopodium quinoa* extract, however, could not achieve the same effects as that of the *Chenopodium formosanum* extract in accordance with the present invention.

The above results indicate that, in comparison with the *Chenopodium quinoa* extract, the *Chenopodium formosanum* extract in accordance with the present invention has a much better effect on increasing the expression of NOS3 gene, increasing the expression of PLAT gene, decreasing the expression of F3 gene and decreasing the expression of SERPINE1 gene. Thus, the *Chenopodium formosanum* extract in accordance with the present invention can be used for at least one of treating cardiovascular diseases, treating hydranencephaly, treating bullous pemphigoid, treating obesity, preventing cardiovascular diseases, preventing hydranencephaly, preventing bullous pemphigoid, preventing obesity, preventing fetal death, and delaying aging, especially for inhibiting thrombosis, decomposing thrombus and/or assisting in regulation of blood pressure.

What is claimed is:

1. A method for preventing or treating at least one of cardiovascular disease, hydranencephaly, bullous pemphigoid and obesity, comprising administering to a subject in need an effective amount of a *Chenopodium formosanum* extract, wherein the extract is a liquid provided by treating a *Chenopodium formosanum* crude extract with at least one of the following steps: (i) centrifuging and (ii) filtering.

2. The method as claimed in claim 1, wherein the *Chenopodium formosanum* crude extract is a water extract of *Chenopodium formosanum*.

3. The method as claimed in claim 1, wherein the *Chenopodium formosanum* extract is administered to the subject by oral administration, intravenous injection, subcutaneous injection, or a combination thereof.

4. The method as claimed in claim 2, wherein the *Chenopodium formosanum* extract is administered to the subject by oral administration, intravenous injection, subcutaneous injection, or a combination thereof.

* * * * *